(12) United States Patent
Blay et al.

(10) Patent No.: US 7,414,024 B2
(45) Date of Patent: Aug. 19, 2008

(54) PROTEINS WITH IL-6 INHIBITING ACTIVITY

(75) Inventors: Jean-Yves Blay, Frontonas (FR); Laurent Alberti, L'Arbresle (FR)

(73) Assignees: Universite Claude Bernard Lyon 1, Villeurbanne (FR); Centre Leon Berard, Lyon (FR); Institut National de la Sante et de la Recherche Medicale - I.N.S.E.R.M., Paris (FR); Hospices Civils de Lyon, Lyons (FR)

( * ) Notice: Subject to any disclaimer, the term of this patent is extended or adjusted under 35 U.S.C. 154(b) by 158 days.

(21) Appl. No.: 10/496,793

(22) PCT Filed: Dec. 4, 2002

(86) PCT No.: PCT/FR02/04171

§ 371 (c)(1),
(2), (4) Date: Nov. 30, 2004

(87) PCT Pub. No.: WO03/048205

PCT Pub. Date: Jun. 12, 2003

(65) Prior Publication Data

US 2005/0158317 A1 Jul. 21, 2005

(30) Foreign Application Priority Data

Dec. 4, 2001 (FR) .................................. 01 15623

(51) Int. Cl.
*A61K 38/00* (2006.01)
*A61K 45/00* (2006.01)
*C07K 17/00* (2006.01)

(52) U.S. Cl. ............................ 514/12; 424/85.2; 514/2; 530/350; 530/351

(58) Field of Classification Search ........................ None
See application file for complete search history.

(56) References Cited

U.S. PATENT DOCUMENTS 5,723,120 A 3/1998 Brakenhoff et al.

FOREIGN PATENT DOCUMENTS

| WO | 94 19004 | 9/1994 |
| WO | 95 13393 | 5/1995 |
| WO | 97 10338 | 3/1997 |

OTHER PUBLICATIONS

Chung et al., Specific inhibition of Stat3 signal transduction by PIAS3, 1997, Science, vol. 278, pp. 1803-1805.*
Alberti et al., IL-6 as an intracrine growth factor for renal carcinoma cell lines, 2004, International Journal of Cancer, vol. 111, pp. 653-661.*
Dermer, Another anniversary for the war on cancer, 1994, Biotechnoloy, vol. 12, p. 320.*
Jain, Vascular and interstitial barriers to delivery of therapeutic agents in tumors, 1990, Cancer and Metastasis Reviews, vol. 9, p. 253-266.*
Zips et al., New anticancer agents: in vitro and in vivo evaluation, 2005, In Vivo, vol. 19, pp. 1-8.*
Wlaschek et al, UVA-Induced Autocrine Stimulation of Fibroblast-Derived Collagenase by IL-6: etc., vol. 101, No. 2, 1993, pp. 164-168.
Arcone et al, Internal Deletions of Amino Acids 29-42 of Human Interleukin-6 IL-6, etc., vol. 288, No. 1-2, 1991, pp. 197-200.
Brakenhoff et al, Analysis of Human IL-6 Mutants Expressed in *Escherichia coli.*, vol. 143, No. 4, 1989, pp. 1175-1182.

* cited by examiner

*Primary Examiner*—Manjunath Rao
*Assistant Examiner*—Ian Dang
(74) *Attorney, Agent, or Firm*—Dennison, Schultz & MacDonald

(57) ABSTRACT

The subject of the present invention concerns proteins with IL-6 inhibiting activity and thier use, and the use of proteins containing at least the amino acid seqeunce SEQ ID NO. 4 as medicianl product, in paritcular as anti-cancerous agent.

3 Claims, 10 Drawing Sheets

FIG.1

PROTEINS WITH IL-6 INHIBITING ACTIVITY

This application is a 371 of PCT/FR02/04171, filed on Dec. 4, 2002.

The invention relates to novel proteins with interleukin 6 (IL-6) inhibiting activity, the genetic engineering tools for their production, namely a recombinant DNA, an expression vector carrying this recombinant DNA, the prokaryote microorganisms and eukaryote cells containing this recombinant DNA, and a drug which can be used in particular as antitumour agent containing one of these proteins as active ingredient.

IL-6 belongs to the family of cytokines. This glycoprotein (SEQ ID NO. 1) has a peptide signal of 28 amino acids, which is cleaved on secretion to give a protein of 184 amino acids (E. Sporeno et al., Blood, 1996, 11, 4510-4519), and is produced by a very wide range of normal or transformed cells, T or B lymphocytes for example, monocytes, macrophages, fibroblasts . . .

IL-6 is encoded by a gene of 5 Kb made up of 5 exons (SEQ ID NO. 2) and located on human chromosome 7.

Brakenhoff et al. report work on fractionated deletions at the N-terminal of IL-6 in their article published in The Journal of Immunology, 1989, 143(4), 1175-1182. Different clones or mutants having short deletions, of no more than 35 amino acids at the N-terminal, are prepared in a prokaryote system and under denaturing conditions. Based on their results, the authors conclude that amino acids 31 to 34 form an important region for the biological activity of IL-6 and that they take part in the conformation of IL-6 enabling its fixing onto one of its receptors. The authors researched an antagonist activity of IL-6 for the mutants prepared on the proliferation of B9 cells and indicate that that they were unable to evidence the same (page 1180 column 2 line 43).

The splicing of the mRNA of IL-6 was studied in particular by Kestler et al. In their article, Blood 1995, 86(12), 4559-4567, the splicing of the second exon of the mRNA of IL-6 leads to deletion of adenine located at the start of exon three of the mRNA of IL-6. In addition, no IL-6 inhibiting activity is reported for the protein derived from the translation of this spliced mRNA.

It is of interest, however, to find means for modulating and especially for inhibiting the IL-6 activity involved in the proliferation of tumour cells in particular.

In surprising manner, the inventors have shown that the protein of sequence SEQ ID NO. 4 corresponding to the translation of the mRNA of IL-6 initiated from the second ATG of exon 3 has IL-6 inhibiting activity.

The subject matter of the invention is therefore this protein having the sequence SEQ ID NO. 4.

A further subject of this invention concerns the proteins corresponding to SEQ ID NO.4 with a polyhistidine tail at the C or N-terminal, which also behave as IL-6 inhibitors, respectively called:

PAC3 which has the sequence SEQ ID NO. 3 and corresponds to SEQ ID NO. 4 to which a tyrosine followed by a polyhistidine tail has been added at the C-terminal, and PAC3Bis which has the sequence SEQ ID NO. 19 and which corresponds to SEQ ID NO. 4 to which a methionine and a lysine followed by a polyhistidine tail and a glutamine have been added at the N-terminal.

The inventors have evidenced that the amino acid sequence SEQ ID NO. 4 makes it possible to obtain inhibition of IL-6 activity. The subject of the invention is therefore the use of a protein comprising at least the amino acid sequence SEQ ID NO. 4 for the fabrication of a drug intended to inhibit IL-6 activity, and in particular of anti-cancer agents.

A further subject of this invention is any nucleic acid which comprises or consists of a chain of nucleotides coding for the proteins of the invention (SEQ ID NO. 3, SEQ ID NO. 4 and SEQ ID NO. 19). They may be sequences of natural or artificial origin, and in particular genomic DNA, cDNA, mRNA, hybrid sequences or synthetic or semi-synthetic sequences. This nucleic acid may be of human, animal, plant, bacterial, viral origin . . . It may be obtained by any technique known to persons skilled in the art, in particular library screening, chemical synthesis or further by mixed methods including the chemical or enzymatic modification of sequences obtained from library bank screening. Advantageously, the nucleic acid of the invention is a cDNA.

The nucleic acids of the invention may, in particular, be prepared by chemical synthesis and genetic engineering using techniques well known to persons skilled in the art and described for example in SAMBROOK et al. "Molecular Cloning: a Laboratory Manual" published in 1989 by Cold Spring Harbor Press, NY, $2^{nd}$ edition.

For example, the synthesis of the cDNA sequences of the invention may be conducted by amplifying mRNAs of human cells using the PCR method ("Polymerase Chain Reaction"), as described for example by GOBLET et al. (Nucleic Acid Research, 17, 2144, 1989) using synthetic oligonucleotides as primers, defined from the DNA sequence SEQ ID NO.2 of IL-6.

Suitable primers for the synthesis of the PAC3 protein are, for example, the following oligonucleotides:

- 5' primer
SEQ ID N° 7:    CCT TGG ATC CAT GGC TGA AAA AGA TGG creates a BamHI restriction site at 5' of the second ATG of exon three of the IL-6 gene

- 3' primer
SEQ ID N° 8:    GGG GAA TTC TAG TGA TGG TGA TGG TGA

TGG TAC ATT TGC CGA AGC CCC silences the stop codon of the IL-6 gene then creates a tail of six histidines with a stop codon and an EcoRI restriction site on the stop codon of the IL-6 gene The amplified fragment of nucleic acids can then be cloned using the techniques described in AUSUBEL et al. (Current Protocols in Molecular Biology, Green Publishing Associates and Wiley Interscience, New-York, 1989, Updated until 1997, chapter 3).

The proteins of the invention may be obtained using the genetic engineering technique comprising the steps of:

culture of a transformed micro-organism or of eukaryote cells transformed using an expression vector carrying a nucleic acid sequence of the invention; and recovering the protein produced by the said micro-organism or the said eukaryote cells.

This technique is well known to persons skilled in the art. For more details thereof, reference may be made to the work: Recombinant DNA Technology I, Editors Ales Prokop, Raskesh K Bajpai; Annals of the New-York Academy of Sciences, volume 646, 1991.

They may also be prepared by conventional peptide synthesis methods well known to persons skilled in the art.

A further subject of the invention concerns prokaryote micro-organisms and eukaryote cells transformed using an expression vector containing a DNA sequence of the invention. This expression vector which may, for example, be in the form of a plasmid, cosmid or phage must, in addition to the DNA sequence of the invention, contain the necessary means for its expression, such as in particular a promoter, a transcription terminator, a replication origin and preferably a selection marker. The transformation of micro-organisms and eukaryote cells is a technique well known to persons skilled in the art who may without difficulty, in relation to the micro-organism to be transformed, determine the means necessary for expression of the DNA sequence of the invention.

As prokaryote micro-organism, E. coli may be cited and as eukaryote the yeast Saccharomyces cerevisiae.

As examples of eukaryote cells suitable for the purposes of the invention, particular mention may be made of COS monkey cells, CHO chinese hamster ovary cells, SfP insect cells, the Jurkat human-T lymphoma line etc., all of these being ATCC listed.

Advantageously, a system may be applied using a vector of baculovirus type. With this system it is possible to produce proteins foreign to the cells (Sf9 cells) of an insect (Spodoptera Frugiperda) using in vivo recombination between a transfer vector (plasmid) which contains the foreign DNA sequence, and the genome of a virus. (O'Reilly, D., L. K. Miller, and V. A. Luckow. 1992. Baculovirus expression vectors: A Laboratory manual. W.H. Freeman and Compan, New York, N.Y.)

A further subject of the invention concerns prokaryote micro-organisms and eukaryote cells co-transformed with expression vectors containing the DNA sequence encoding the protein of the invention, said expression vectors also containing means suitable for their expression, including in the yeast double-hybrid system.

A further subject of he invention concerns transgenic animals expressing a transgene of the PAC3, PAC3Bis protein or the protein of SEQ ID NO. 4 of the invention.

These transgenic animals may be used as in vivo models to study cell cycle disturbance and proliferation through the absence or overexpression of the gene of the protein of the invention, or truncated or mutant forms of this protein.

These transgenic animals are obtained using techniques well known to persons skilled in the art, such as those described in: Manipulating the mouse embryo: a laboratory manual, HOGAN B., BEDDINGTON R., COSTANTINI F. & LACY E. Cold Spring Harbor laboratory press, second edition, 1994.

The preferred animals are mammals such as the mouse or rat.

Yet a further subject of the invention concerns novel antibodies, preferably monoclonal, directed against the PAC3, PAC3Bis protein or the protein of SEQ ID NO. 4.

These antibodies may be monoclonal antibodies obtained using the well known method of KOHLER and MILSTEIN (Nature, 256, 495-497, 1975) or polyclonal antibodies obtained using conventional animal immunisation methods (Antibodies, a laboratory manual, E. Harlow & D. Lane, Cold Spring Harbor laboratory press, 1988).

The antisense oligonucleotides blocking the transcription or translation of the proteins of the invention which hybridize with a nucleic acid sequence such as previously defined, also form a further subject of the invention.

These antisense oligonucleotides are prepared using techniques well known to persons skilled in the art, such as those described by AUSUBEL et al. (Current Protocols in Molecular Biology, supra.)

The protein of sequence SEQ ID NO. 4, the PAC3 protein, PAC3Bis protein, and any protein containing the sequence SEQ ID NO. 4 are of particular interest from a therapeutic viewpoint. Their therapeutic activity is connected more particularly with their ability to inhibit IL-6 activity. These proteins will be of particular use as anti-inflammatory agent to treat any inflammatory or infectious pathology in which IL-6 is shown to play a physiopathological role, for the treatment of diseases in which it is necessary to inhibit the proliferation of benign or malignant tumour cells whose growth is stimulated by IL-6, or to induce the death of cells whose survival is IL-6-dependent, or further to inhibit the metastatic dissemination of tumour cells whose dissemination is induced by IL-6, in autocrine, paracrine or endocrine manner, in particular lymphomas, leukemias, myelomas, carcinomas, sarcomas, Kaposi sarcomas, Caspelman's disease in patients suffering from malignant tumours; in which it is necessary to inhibit the protective effect of IL-6 on the death of tumour cells induced by cytotoxic (chemical, biological or physical) or cytostatic agents; in which it is necessary to inhibit the proinflammatory, cachectising and regulating properties of IL-6 hematopoiesis resulting from abnormal production of this protein, in particular autoimmune chronic inflammatory syndromes (polyarthritis, systemic lupus erythematosus), in connective-tissue diseases, in serious infections, for example of viral or bacterial type associated with hyperproduction of IL-6 in benign or malignant tumours of haematological, epithelial, conjunctive origin, for example; in which it is necessary to inhibit bone changes, IL-6-induced osteolysis in particular, in degenerative, inflammatory or tumoral diseases for example; in which it is necessary to inhibit the immunological properties of IL-6 (immunostimulant or immunosuppressive) in clinical situations in which the deregulation of IL-6 production plays a physiopathological role, in particular autoimmune syndromes, infectious diseases and neoplastic disorders of leukaemia, myeloma, carcinoma or sarcoma type.

The invention also concerns the protein of sequence SEQ ID NO. 4, the PAC3 protein, the PAC3Bis protein, and any protein containing the sequence SEQ ID NO. 4 for their use as therapeutic agent and pharmaceutical compositions containing the protein of sequence SEQ ID NO. 4, the PAC3 protein, the PAC3Bis protein, or any protein containing the sequence SEQ ID NO. 4, in association with at least one suitable pharmaceutical excipient.

These pharmaceutical compositions are prepared following conventional techniques well known to persons skilled in the art. The pharmaceutical excipients are chosen in relation to the desired pharmaceutical form and administering mode, for example oral, sublingual, sub-cutaneous, intramuscular, intra-venous, topical administration . . . For example, the protein or peptide fragments of the invention may be formulated in injectable form, in association with one or more pharmaceutically acceptable excipients and in a physiologically acceptable solvent such as water or saline solution. Each unit dose may, for example, contain between 10 and 500 mg active ingredient to obtain the desired therapeutic or prophylactic effect.

A further subject of the invention is the use of the protein of sequence SEQ ID NO. 4, of the PAC3 protein, the PAC3Bis protein, or of any protein containing the sequence SEQ ID NO. 4 for the preparation of anti-tumoral or anti-cancer drugs and in particular intended to prevent or treat IL-6 dependent diseases, especially the aforesaid diseases and more particularly lymphomas, leukemias, myelomas, carcinomas, sarcomas.

The invention will now be described in detail with the help of the following experimental reports.

A major part of the techniques described in these examples, well known to persons skilled in the art, is set forth in the work by SAMBROOK et al. (supra) or in the publication of AUSUBEL et al. (supra).

The following description will be more readily understood with the help of FIGS. 1 to 10 in which:

FIG. 1 shows the alignment of sequences obtained using primers SEQ ID no 5 to no 16 on the KAE15.8 vector, FIG. 2 is a map of the transfer plasmid of the PAC3 protein, FIG. 3 gives the chromatography profile used for purification of the PAC3 protein, FIG. 4A shows the PAC3 protein developed by silver colorimetry, FIG. 4B shows Western blot characterization of the PAC3 protein detected by an anti-histidine body and developed by chemiluminescence, FIGS. 5A, 5B, 5C give the results obtained with the PAC3 protein on the inhibition of U266 cell proliferation, FIG. 6 gives the results obtained with the PAC3 protein on the differentiation of CD34+ progenitors, FIG. 7 is the chromatography profile used for the purification of the PAC3Bis protein.

Figure 10:
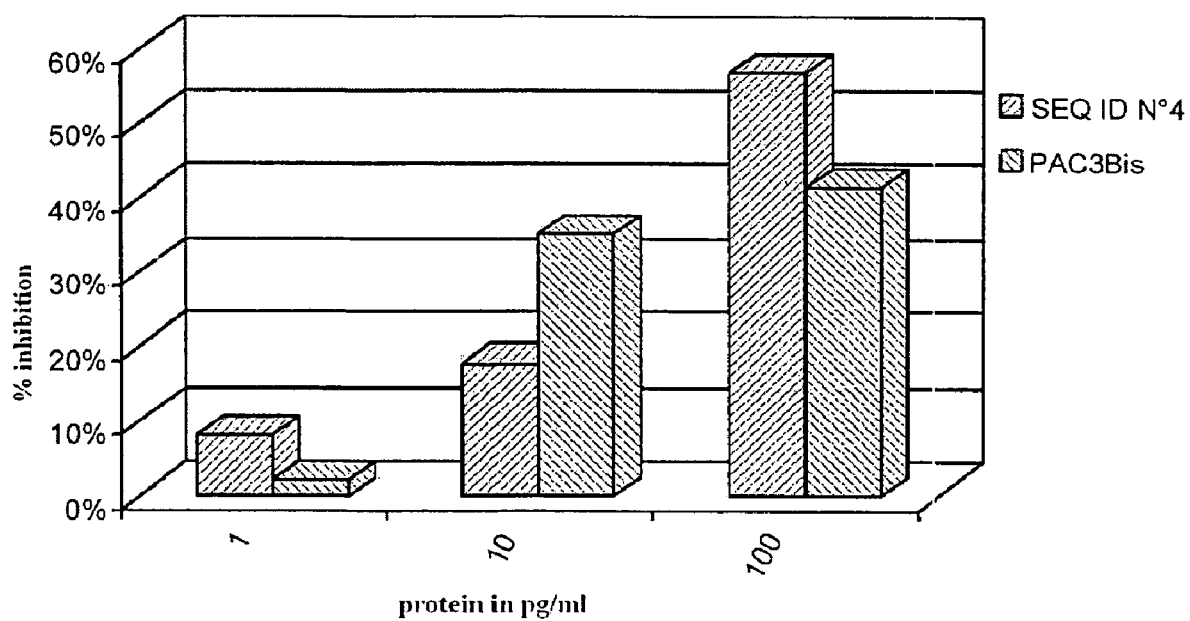

FIG. 10 gives the results obtained with the PAC3Bis protein and the protein of sequence SEQ ID NO. 4 on the proliferation of U266 cells.

A more detailed description follows of a method for producing and purifying the PAC3 protein of SEQ ID no.3 and the proteins of SEQ ID NO. 4 and SEQ ID NO. 19 (PAC3Bis), and the different tests evidencing their biological activity, in particular on the proliferation of the myeloma U266 line.

A—Production and Purification of the PAC3 Protein

A.1—RNA Extraction

A.1.1—RNA Extraction

After culture up to 80% confluence of the CLB-TUG tumoral line (deposited with the CNCM Paris, France on 13 Nov. 2001 under number I-2749, adenocarcinoma cell of fibroblast type produced from a lymphatic gland draining a primary adenocarcinoma tumour in the kidney of a man aged 40 years), the culture medium is removed, then the cells are detached by trypsination to form a dry residue of $10^6$ cells. The cells are then washed three times in phosphate salt buffer (PBS). The cell deposit is then re-suspended in 1 ml TRIzol solution (commercially available from Gibco) and incubated for 5 minutes at room temperature. At the end of this incubation, 0.2 ml water saturated chloroform are added to this suspension. The whole is mixed under vigorous agitation for 15 seconds, then the emulsion is incubated for 5 minutes at room temperature. The different phases are separated by 15-minute centrifuging at 12 000 g and at 4° C. The aqueous phase containing the RNA is transferred into a new tube to precipitate the RNA with 0.5 ml isopropanol. The mixture is incubated for 1 hour at −20° C., then centrifuged for 15 minutes at 12 000 g at 4° C. The RNA residue is washed in 1 ml 75% ethanol then centrifuged for 10 minutes at 12000 g and at 4° C. After removing the ethanol, the residue is solubilized to a concentration of 1 $mg.ml^{-1}$ in a 0.1% water solution of diethylpyrocarbonate (DEPC).

A.1.2—Preparation of Complementary Deoxyribonucleic Acid (cDNA)

For the synthesis of complementary deoxyribonucleic acid (cDNA) the system used is "Expand Reverse Transcriptase" from Boerhinger Manheim (Boerhinger Manheim, Meylan, France) following the supplier's recommendations.

20 μl of a 0.1% water solution of DEPC containing 1 μg RNA, 50 pM oligonucleotide (dT) 18 (Genset, Paris, France) are denatured at 65° C. for 10 minutes. At the same time, to a final volume of 20 μl, a solution is prepared comprising 1× Expand reverse buffer, 10 mM DTT, 1 mM of each of the four deoxyribonucleotides (dATP, dCTP, dGTP, dTTP), 20 IU Rnase inhibitor and 50 IU Expand Reverse. The two solutions are mixed and incubated for 60 minutes at 42° C.

A.2—PCR (Polymerase Chain Reaction)

A.2.1—PCR Primers

The primer pairs used for the PCRs are the following:

First primer pair:

```
- 5' primer
SEQ ID N° 5:

GAG AAG CTT TAG CGG CCG CCC AGG AGC CCA GCT
``` creates a BamHI restriction site at 5' of the second ATG of exon three of the IL-6 gene.

```
3' primer
SEQ ID NO 6:  GAA TGC CCG GGA AAC TCG AGA ATC TGA

GGT GCC C
``` creates a Sma I restriction site at 3' of the stop codon of the IL-6 gene.

Second primer pair:

```
5' primer
SEQ ID NO 7:  CCT TGG ATC CAT GGC TGA AAA AGA TGG
``` creates a BamHI restriction site at 5' of the second ATG of exon three of the IL-6 gene.

```
- 3' primer
SEQ ID N° 8:    GGG GAA TTC TAG TGA TGG TGA TGG TGA

TGG TAC ATT TGC CGA AGC CCC
``` silences the stop codon of the IL-6 gene then creates a tail of six Histidines with a stop codon and a EcoR I restriction site on the stop codon of the IL-6 gene.

Sequencing Primers:

```
SEQ ID N° 9:         AGC TAT GAA CTC CTT CTC C
``` sequence primer starting from base 30 in the reading direction of the IL-6 gene.

SEQ ID N° 10:    GTT CTG AAG AGG TGA GTG GC sequence primer starting from base 187 on the complementary strand of the spliced IL-6 gene.

SEQ ID N° 11:    AGG TAT ACC TAG AGT ACC TCC sequence primer starting from base 401 in the reading direction of the IL-6 gene.

SEQ ID N° 12:    AAC TCG AGA ATC TGA GGT GC sequence primer starting from base 697 on the complementary strand of the IL-6 gene.

SEQ ID N° 13:    TCG AGG TCG ACG GTA TC sequence primer hybridizes at 5' of the multiple cloning site of the KS+ plasmid.

SEQ ID N° 14:    GCG AGA TCT TGA TCA CCT AG sequence primer hybridizes at 3' of the multiple cloning site of the KS+ plasmid.

SEQ ID N° 15:    GTA ATA CGA CTC ACT ATA GGG C sequence primer hybridizes at 5' of the multiple cloning site of the KS+ plasmid.

SEQ ID N° 16:    GCT TGT TCC TCA CTA CTC TC sequence primer starting from base 258 on the complementary strand of the IL-6 gene.

A.2.2—PCR Amplification of cDNAs

1 µg cDNA solution to be tested is added to 25 µl of a solution containing 0.2 mM dNTP (Promega, Lyon, France) and 300 nM of each of the chosen two primers (SEQ ID NO. 5 and NO. 6). Extemporaneously to the PCR reaction, 25 µl of a solution containing 100 mM KCl, 20 mM Tris-HCl (pH=7.5), 0.5% Tween 20, 1.5 mM $MgCl_2$, 2.6 U Expand Polymerase (Boehringer) are then added to the first 25 µl. The PCR cycles and the hybridization temperatures vary in relation to the primers used as shown in TABLE 1.

TABLE 1

| Primers | Concentration | Cycles |
| --- | --- | --- |
| SEQ ID N° 5 | 7.5 nm/ml | 30 minutes at 94° C. |
| SEQ ID N° 6 | | 30 minutes at 58° C. |
| | | 45 minutes at 72° C. |
| | | 35 cycles |
| SEQ ID N° 7 | 7.5 nm/ml | 30 minutes at 94° C. |
| SEQ ID N° 8 | | 30 minutes at 58° C. |
| | | 45 minutes at 72° C. |
| | | 35 cycles |

Each PCR starts with denaturing for 2 minutes at 94° C. and ends with elongation for 7 minutes at 72° C.

From the fifteenth to the thirty-fifth cycle, the elongation time is increased by 20 seconds per cycle.

PCR is conducted in an Eppendorf gradient thermo cycle apparatus (Merck, Strasbourg, France). The PCR reaction products are analyzed on 1% agarose gel in TBE (45 mM Tris bases, 10 mM EDTA).

A.2.3—Purification of PCR Fragments

The PCR products are purified with Wizard by Promega, from a 0.1% agarose gel in TAE buffer (40 mM Tris-HCl, 1 mM EDTA). After migration, the bands of interest with no contaminant material are sampled using a sterile scalpel. The gel containing the DNA is excised under U.V. The gel piece is incubated for 5 minutes at 65° C. in 1 ml resin solution. This solution is recovered through a filter, then washed with 2 ml 80% isopropanol. After centrifugation (30 seconds at 12000 g), the purified DNA is hydrated with 40 µl water, then eluted by centrifugation (30 seconds at 12 000 g).

A.2.4—Cloning of the PCR Product

After purification, the PCR bands must be cloned in a plasmid, for their amplification, thereby enabling their sequencing and sub-cloning in different expression plasmids. Using PCR, two restriction sites (HinD III at 5' and Sma I at 3') were created allowing the cloning of the fragment in the multiple cloning site of the "Blue script" $SK^+$ plasmid (Startagene, Ozyme, Montigny, France).

1 µg DNA is left to digest for 4 hours at 25° C. in a solution containing 50 mM $K(C_2H_3O_2)$, 20 mM Tris (pH=7.9), 10 mM $Mg(C_2H_3O_2)_2$, 1 mM DTT and 80 U Sma I enzyme (Biolabs, Ozyme, Saint Quentin en Yvelines, France). 10 U of HinD III enzyme are then added, and the solution is incubated for 12 hours at 37° C. At the same time, 0.5 µg of $SK^+$ plasmid are similarly digested.

The digestion products are purified with the Compass kit (American Bioanalytical, Natick, USA). The DNA is diluted in 3 volumes of a saline solution (supplied with the kit) to which are added 5 µl silane matrix. After 5 minutes' incubation at room temperature, the solution is centrifuged (30 s. at 12000 g). The residue resin is washed with 1 ml wash solution (supplied with the kit) which is then removed by two successive centrifugations of 30 seconds at 12000 g. After 5 minutes at room temperature, the resin is re-suspended in 12 µl water. After incubating for 5 minutes at 65° C., the suspension is centrifuged for 1 minute at 12 000 g, to collect the supernatant containing the DNA.

The digested, purified fragment and the plasmid are incubated in a solution containing 50 mM Tris (pH=7.8), 10 mM $MgCl_2$, 10 mM DTT, 1 mM ATP, 50 mg.$ml^{-1}$ BSA and 24000 U of T4 ligase (Biolabs). The solution is incubated for 16 hours at 4° C.

The ligation solution is then transformed in a competent JM109 bacterium (Promega), to obtain a sufficient quantity of plasmid enabling the sequencing of the PCR product inserted in the plasmid.

A.2.5—Sequencing and Sequence Analysis

Sequencing of the insert is performed using a 373A Applied Biosystem automatic sequencer (Roissy, FRANCE). The principle of automatic sequencing is based on laser determination of a succession of fluorescent bases incorporated in DNA strands neosynthesized from the control sequence by PCR.

With this PCR, and from the primers chosen from TABLE 2 below in relation to the sequence to be analysed, DNA brands are synthesized in which fluorescent bases are incorporated during synthesis of the complementary strand.

TABLE 2

| Primers | Concentration | Cycles |
|---|---|---|
| SEQ ID N° 9 | 10 µM | 30 seconds at 96° C.<br>30 seconds at 55° C.<br>4 seconds at 68° C.<br>35 cycles |
| SEQ ID N° 10 | 10 µM | 30 seconds at 96° C.<br>30 seconds at 55° C.<br>4 seconds at 68° C.<br>35 cycles |
| SEQ ID N° 11 | 10 µM | 30 seconds at 96° C.<br>30 seconds at 55° C.<br>4 seconds at 68° C.<br>35 cycles |
| SEQ ID N° 12 | 10 µM | 30 seconds at 96° C.<br>30 seconds at 55° C.<br>4 seconds at 68° C.<br>35 cycles |
| SEQ ID N° 13 | 10 µM | 30 seconds at 96° C.<br>30 seconds at 55° C.<br>4 seconds at 68° C.<br>35 cycles |
| SEQ ID N° 14 | 10 µM | 30 seconds at 96° C.<br>30 seconds at 55° C.<br>4 seconds at 68° C.<br>35 cycles |
| SEQ ID N° 15 | 10 µM | 30 seconds at 96° C.<br>30 seconds at 55° C.<br>4 seconds at 68° C.<br>35 cycles |
| SEQ ID N° 16 | 10 µM | 30 seconds at 96° C.<br>30 seconds at 55° C.<br>4 seconds at 68° C.<br>35 cycles |

1 µg of plasmid to be tested, prepared by midi-prep, is added to 20 µl of a solution containing Fs buffer (Applied Biosystem, St Quentin en Yvelines, France) and 0.5 µM of a sequence primer (TABLE 2).

Each PCR starts by denaturing for 3 min at 96° C. and ends with final elongation for 4 min. at a 68° C.

Figure 1:
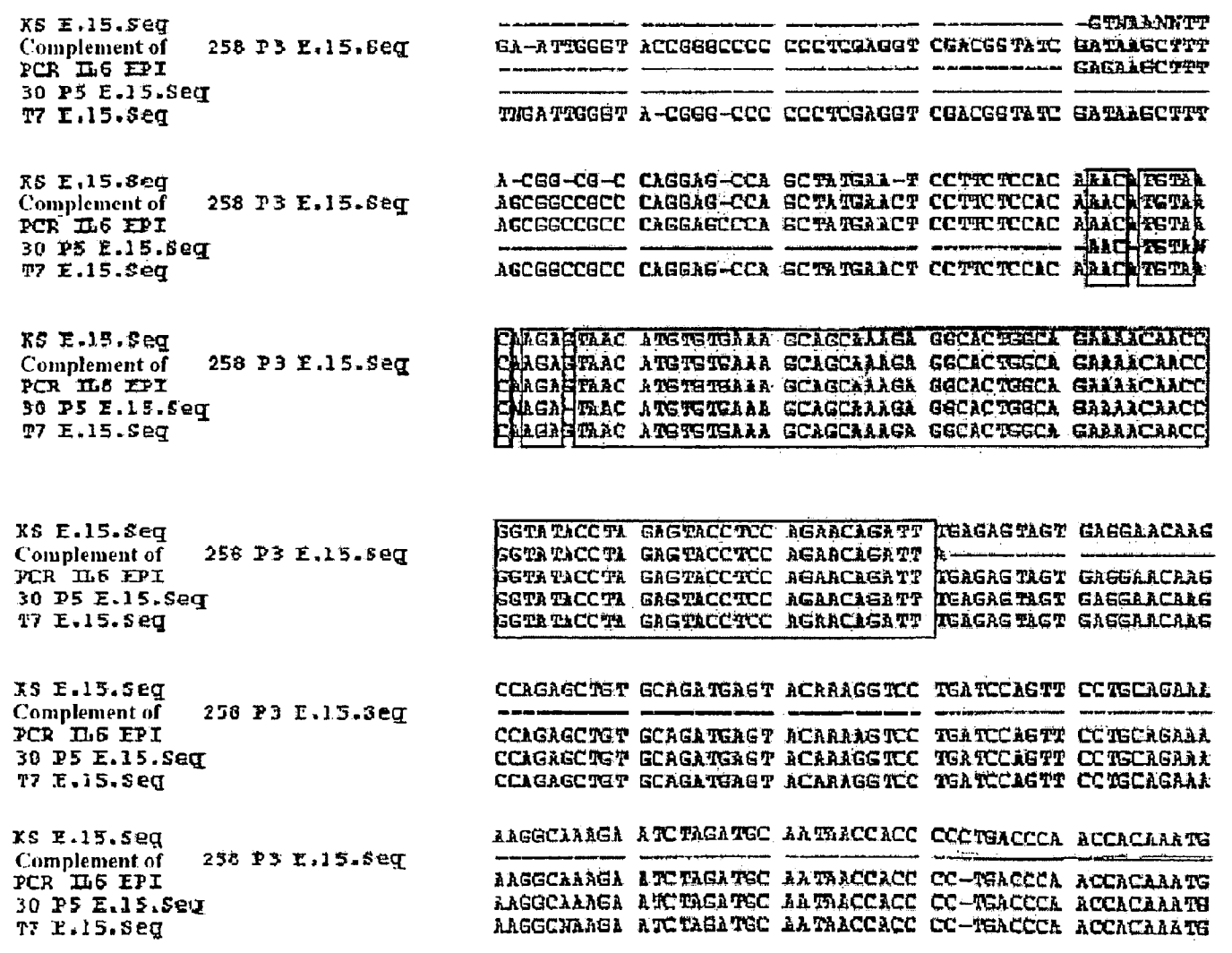
Figure 2:
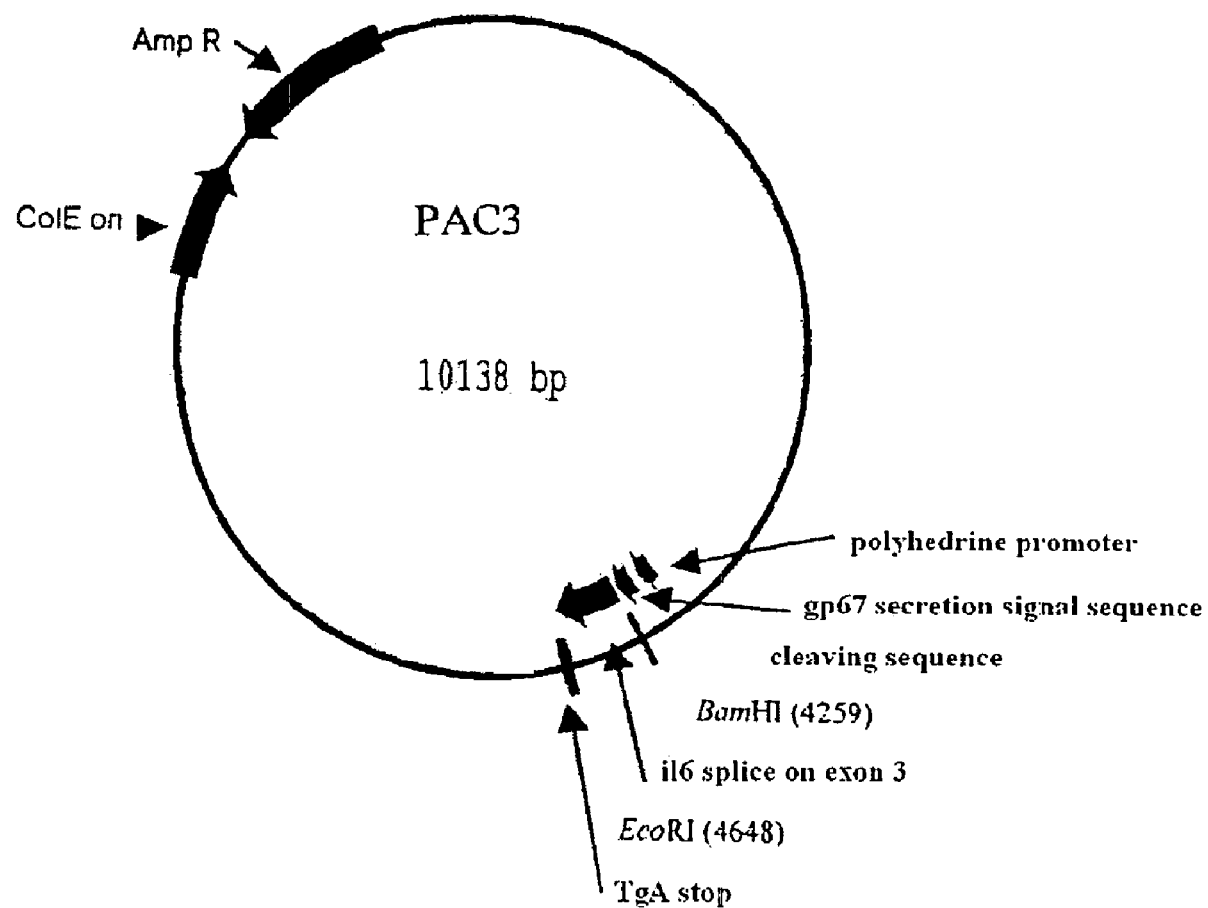

Using Vector NTI software by Informax (Oxford, U.K.), all the sequences obtained with the different primers are aligned using the Vector NTI software by Informax (Oxford U.K.); the alignment is made of all the sequences obtained with the different primers on the KAE15.8 plasmid. With this alignment it is possible to compare the sequences between themselves and in relation to the expected theoretical sequence which is here called PCR IL-6 Epi. The fact that several primers are used to sequence the same insert makes it possible to overcome reading errors by the automatic sequencer. Reference may be made to FIGS. 1 and 2.

This KAE 15.8 plasmid will be used for all the other plasmid constructs.

A.3—Preparation of Baculoviruses

The virus production system used is the Baculogold® transfection Kit (PharMingen, Becton Dickinson, Paris, France). Baculoviruses are prepared in two steps: firstly the transfer vector is constructed and secondly viruses are obtained by homologous recombination between the transfer vector and a linear baculovirus in sf9 cells.

A.3.1—Preparation of the Transfer Vector

On the previously obtained and sequenced KAE15.8 plasmid, a PCR is conducted using the primer pair SEQ ID NO. 5 and SEQ ID NO. 6. The PCR, fragment analysis and their purification is performed as previously described.

The digestion of purified PCR fragments and of the pAcGP67-B transfer plasmid is made with the enzymes BamHI and EcoRI (Biolab) for 4 hours at 37° C. Ligation of the insert is identical to that previously described. The plasmid constructs are then transformed in JM109 and sequenced.

The transfer vectors having the correct sequence are amplified to obtain 1 mg of endonuclease-free plasmid using the EndoFree® plasmid Mega Kits by Qiagen. (Courtaboeuf, France).

This plasmid batch will be used for co-transfection of the transfer vector and of the linear baculovirus in the Sf9 cells. The map of this transfer vector is given in FIG. 2.

A.3.2—Preparation and Selection of the Viruses

The baculoviruses are obtained by co-transfection of a transfer vector and of a linear baculovirus in a Sf9 cell. After homologous recombination, the cell produces replicative virions producing the protein of interest.

A.3.2.1—Co-Transfection $2.10^6$ Sf9 cells are co-transfected with 0.5 µg baculogold and 5 µg transfer vector using calcium sulphate. After 4 hours' incubation at 27° C., the transfection medium is replaced by SF900 II culture medium (Gibco) supplemented with 5% fetal calf serum (Hyclone, Perbio, Bezon, France). After 5 days' incubation at 27° C., the culture supernatant containing the viruses is collected for cloning of the viruses using the plaque assay technique.

A.3.2.2—Cloning of Viral Particles by Plaque Assay

The viral particles are cloned by lysis plaque selection in a gelled medium.

$7.10^6$ Sf9 cells are seeded in a culture dish of 100 mm diameter. A culture dish is prepared by diluting the culture supernatant containing the viral particles. A series of dilutions is performed from $10^{-1}$ to $10^{-6}$ in relation to the viral content of the culture supernatant. The cells are incubated for 1 hour at 27° C. with the dilution, then a 2% Agarplaque solution (prepared in a protein-free culture medium) is poured onto each culture dish. After 10 minutes at room temperature, the entire dish gels trapping the cells in a 1% agarplaque culture medium. The dish with cells is left to incubate for 12 days at 27° C.

Since the virus is blocked by the agarplaque, it can only develop through cell-to-cell contamination forming plaques of cell lysis able to be read unaided. If the viral dilution is sufficient, a lysis plaque corresponds to a virus. The lysis plaques are collected using a pipette cone then transferred into 1 ml culture medium in order to elute the viral particles from the agarose by incubation for 12 hours at 4° C. under agitation.

300 µl of this eluate will infect $5.10^6$ cells in a culture dish 100 mm in diameter in 3 days at 27° C. The culture supernatant is stored at 4° C. and the cells are washed with PBS, residued then lysed so that virus production of the protein of interest can be controlled on SDS-page acrylamide gel (Gibco).

A.3.3—Characterization of the Viruses by SDS-Page Acrylamide Gel $2.10^7$ cells are lysed with 1 ml lysis buffer (10 mM Tris-HCl pH=7.5; 130 mM NaCl; 1% Triton X-100 10 mM NaF; 10 mM NaPi; 10 mM NaPPi; 10 µg/ml phenanthroline; 10 µg/ml aprotinine; 10 µg/ml leupeptine; 1 mM PMSF) for 45 minutes at 4° C. The lysate is then clarified by centrifugation for 45 minutes at 40 000 g.

30 µl of lysate are denatured for 5 minutes at 95° C., in the presence of a charge buffer (2.5% SDS, 5% β-mercaptoethanol, 1 mM Tris pH=7.4, 1 mM EDTA, 20% glycerol, 5% of 1% coomassie blue). The denatured samples undergo electrophoresis for 2 hours at 120 V in a 12% acrylamide SDS gel (Gibco). After migration, the proteins are transferred onto a PVDF membrane (PolyVinyliDene Fluoride by Millipor, Poly-labo, Strasbourg) by wet transfer for 45 minutes at room temperature at 0.350 A in a buffer containing 25 mM Tris-HCl, 192 mM glycine, pH=8.3. For 12% acrylamide gels, 20% methanol is added to this buffer.

The transferred proteins are identified via their poly histidine tail by an anti-histidine monoclonal antibody directly coupled to an alkaline phosphatase (Invitrogen, Gibco, France). These are visualized by a chemiluminescence technique (Tropix, Perkin Elmer).

A.4—Production and Purification of the PAC3 Protein

A.4.1—Production

Production is made by infecting SfP cells in suspension. 1 l of serum-free SF900 culture medium (Gibco) is seeded with $2.10^6$ cells.ml$^{-1}$ and 1 ml of viral suspension with $10^8$ pfu.ml$^{-1}$. They are left to incubate for 4 days at 27° C. under gentle agitation. At the end of the culture, the cells are residued by centrifugation at 10 000 g for 5 minutes and the supernatant is stored at 4° C.

A.4.2—Purification

The first step consists of preparing the sample so that it is compatible with the chromatographic column. A first dialysis is therefore conducted against 20 volumes of 20 mM phosphate buffer, pH=7.4, through a dialysis membrane with a cut-off threshold of 15 KDa. After overnight dialysis at 4° C., under gentle agitation, the dialysate is ready to be purified on a 5 ml Chelate-HITrap affinity column by Pharmacia. This column is packed with sepharose with a graft able to chelate different types of bivalent metals. In this purification the graft contains copper thereby imparting an affinity for poly-histidine chains.

A.4.2.1—Chromatography

The column is mounted on the HR chromatography system by Biorad stabilised at 4° C. in a cold room. The flow rate of the column is limited to 1 ml.min$^{-1}$. with a maximum pressure of 100 psi.

Initially, the column is washed and activated by a first washing with 5 volumes of distilled water, then activated with 0.5 volume of 100 mM copper sulphate solution. The non-fixed copper is removed with 10 volumes of distilled water. The column is stabilized with 10 volumes of 20 mM phosphate buffer, pH=7.4, 1 M NaCl, 10 mM inmidasole.

Purification is conducted using several successive passes to avoid saturating the column.

Each pass starts with stabilisation of the U.V. base line at 280 nm using 2 volumes of 20 mM phosphate buffer, pH=7.4, 1 M NaCl, 10 mM imidazole, then 4 volumes of dialysate are injected. Several washings are performed with 6 volumes of 20 mM phosphate buffer, pH=7.4, 1 M NaCl, 10 mM imidazole and 6 volumes of 20 mM phosphate buffer, pH=7.4, 1 M NHCl$_4$.

The proteins are eluted from the column using 4 volumes of a linear gradient, 0% to 60% of 20 mM phosphate buffer, pH=7.4, 500 mM NaCl, 50 mM EDTA. At the end of elution the column is washed with 6 volumes of 20 mM phosphate buffer, pH=7.4, 1 M NHCl$_4$.

Figure 3:
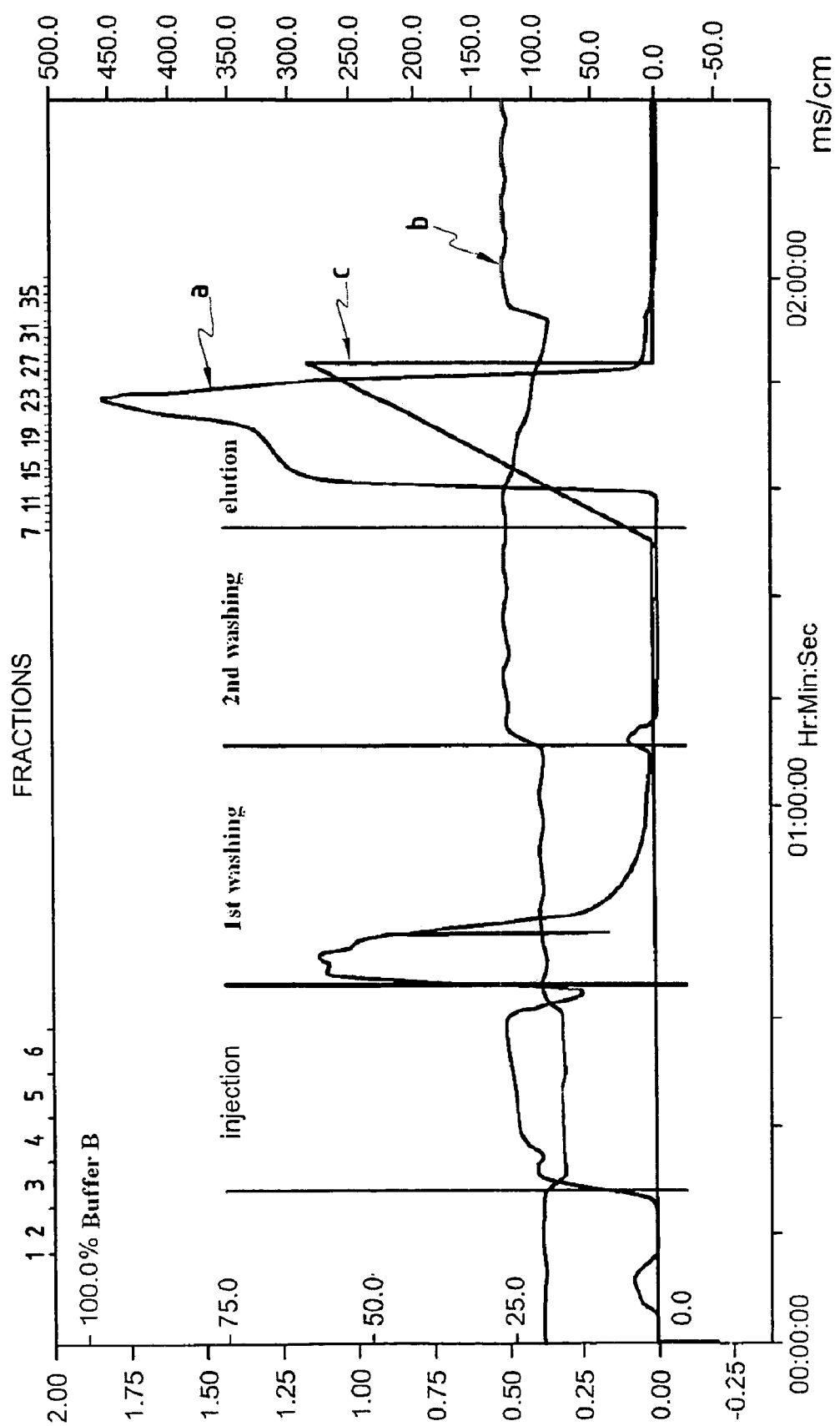

At this stage the column may be activated for a further pass. FIG. 3 gives the chromatography tracing: curve a shows protein absorbance at 280 nm, curve b shows the conductivity of the injected solutions, curve c the percentage of elution solution.

So that the protein can be used in cell culture, the eluate is firstly concentrated using Centricon plus-20 (Amicon, Millipor, France) having a 10 Kda separation membrane, then dialysed against 30 volumes PBS without $Mg^{2+}$ and $Ca^{2+}$ through a dialysis membrane having a cut-off threshold of 15 Kda. After overnight dialysis at 4° C., under gentle shaking, the protein can be concentrated using Centricon plus-20. The solution is then stored at −20° C.

A fraction of the protein is deposited in duplicate on SDS-page 12% acrylamide gel and left to migrate as described previously. Part of the gel is transferred onto a PVDF membrane to develop the proteins by chemiluminescence using an anti-histidine body, the other part is silver stained using a Biod-rad silver kit to obtain the complete panel of proteins present in the sample.

Figure 4A:
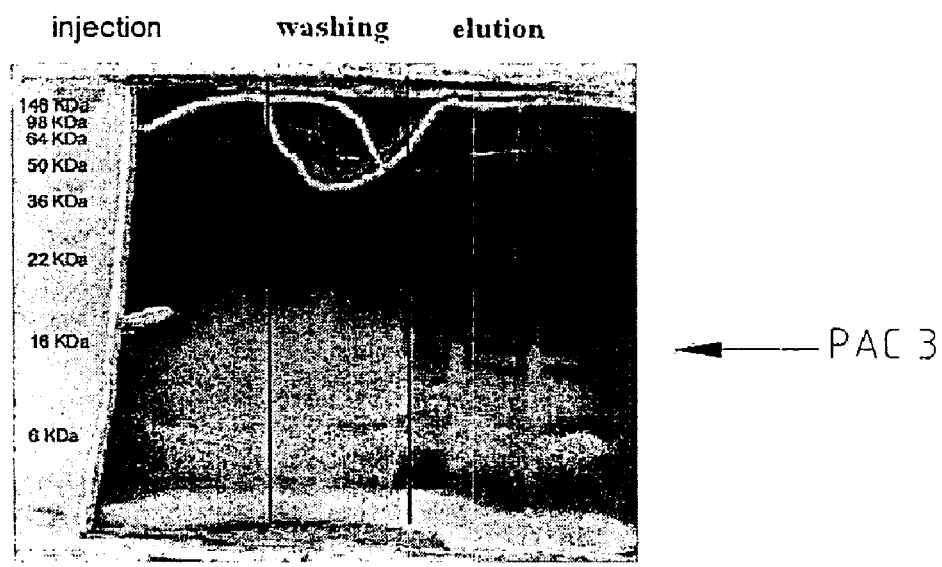
Figure 4B:
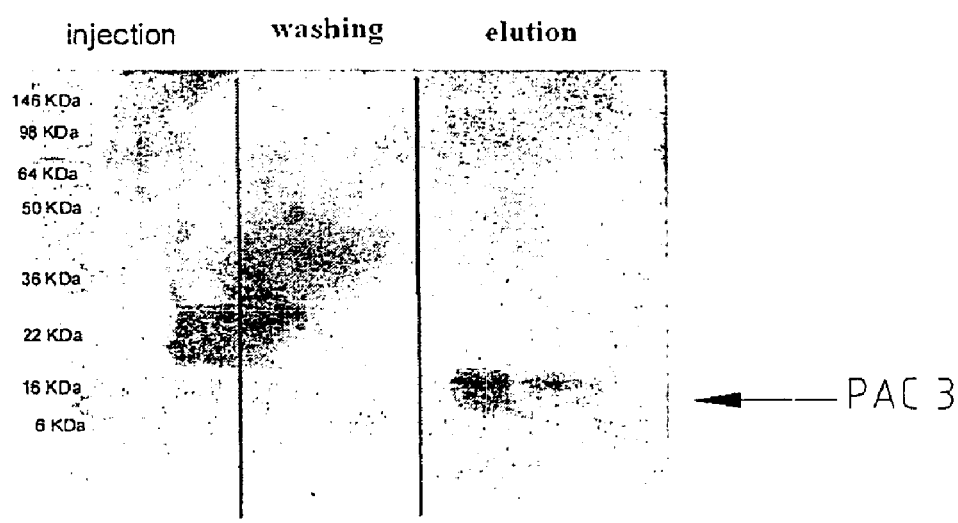

The PAC3 protein thus isolated and purified has, at the C-terminal, a poly-Histidine tail and is of sequence SEQ ID NO. 3. Reference may be made to FIGS. 4A and 4B which show the PAC3 protein of 16 KDa weight.

B—Biological Activity of the Pac3 Protein

B.1—Inhibition of the Proliferation of Tumour Lines for which IL-6 has a Mitogenic Effect B.1.1—Choice of Lines and Assessment of their Proliferation.

The cells are seeded at $2.5.10^5$ cells.ml$^{-1}$ in RPMI 1640 medium (Gibco) supplemented with 2 mM L-glutamine, 100 IU.ml$^{-1}$ penicillin and 100 U.ml$^{-1}$ streptomycin. 100 μl of this cell suspension are "weaned" 24 hours at 37° C. (5% $CO_2$ under humic atmosphere) in a 96-well dish. After "weaning", the culture medium is replaced by the solution to be tested diluted in culture medium (RPMI 1640 supplemented with 2 mM L-glutamine, 100 IU.ml$^{-1}$ penicillin, 100 U.ml$^{-1}$ streptomycin and 20% fetal calf serum). The whole is left to incubate 24, 48 or 72 h (37° C. at 5% $CO_2$ under humic atmosphere) in accordance with handling conditions. Cell proliferation is determined by incorporation of tritiated thymidine.

U266 is a myeloma line; it is clearly established that in this model IL-6 plays an autocrine role in proliferation and that the cell expresses large quantities of gp 80 and gp 130 receptors on its cell surface (contrary to kidney adenocarcinoma lines which do not express gp 80 on their surface).

B.1.2—Results

B.1.2.1—Activity of the PAC3 Protein of SEQ ID NO. 3 on the Proliferation of the U266 Line The negative control used is a baculovirus production coding for a non-pertinent protein (a catechol-degrading enzyme, ref pAcHLT-XylE "PAC-XylE" control vector by Pharmigen) purified under the same conditions as the PAC3 protein of the invention.

Figure 5A:
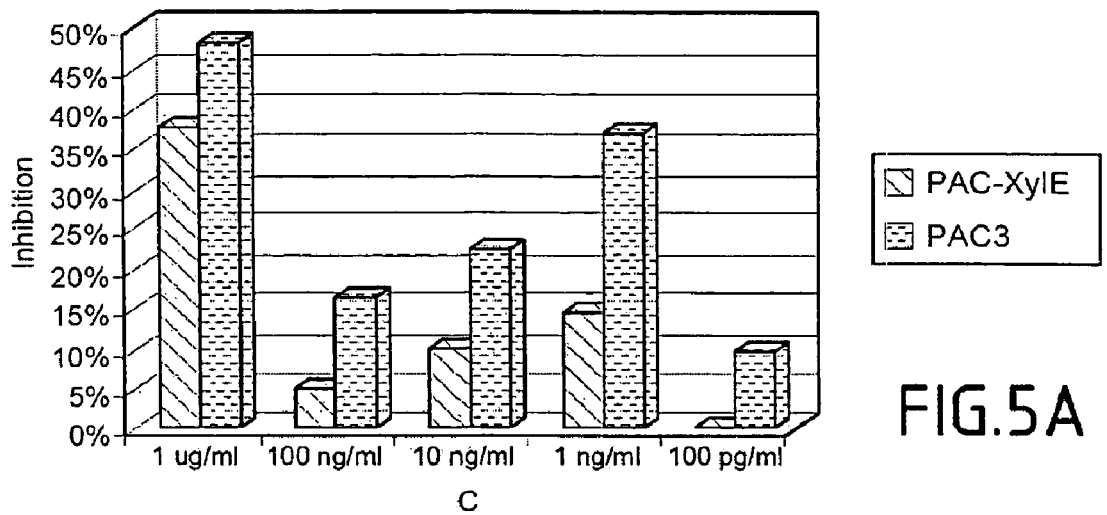

FIG. 5A shows developments, relative to protein concentration (c), in the percentage inhibition of U266 proliferation without activation, in the presence of the PAC3 protein.

Figure 5B:
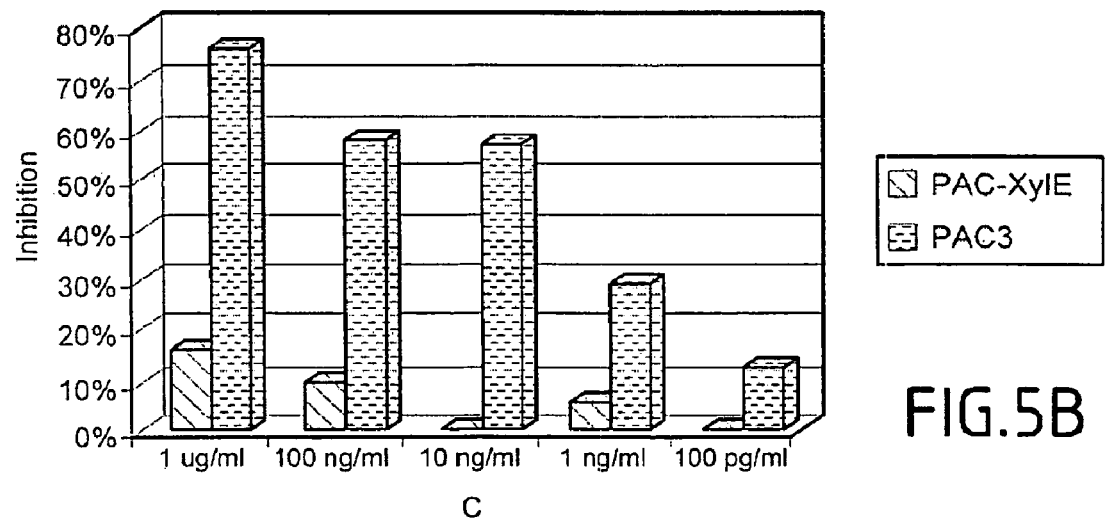

FIG. 5B shows developments, relative to protein concentration (c), in the percentage inhibition of U266 proliferation with activation by 1.26 pg/ml IL-6 in the presence of the PAC-3 protein.

Figure 5C:
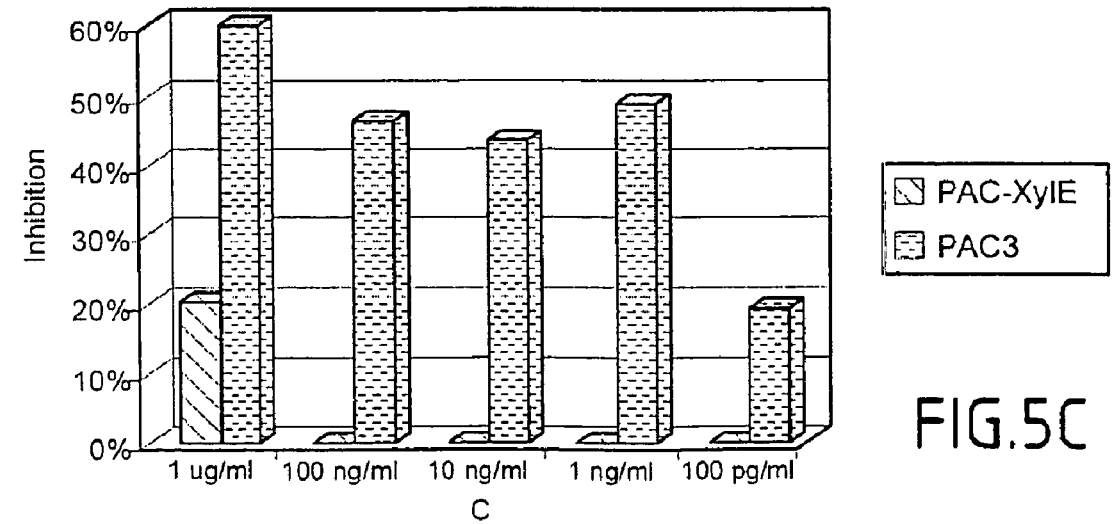

FIG. 5C shows developments, relative to protein concentration (c), in the percentage inhibition of U266 proliferation with activation by 12.6 pg/ml IL-6 in the presence of the PAC-3 protein.

A shown by the graphs in FIGS. 5A, 5B and 5C, with the PAC3 protein, proliferation inhibition of up to 25% is obtained compared with the control. The limited nature of this inhibition probably results from a mainly intracrine functioning mode of IL-6 in this line, not involving the IL-6 receptors expressed on the cell surface.

However, the magnitude of this inhibition specifically induced by the PAC3 protein of the invention, is increased when the cells are cultured in the presence of exogenous IL-6, reaching 60% of the proliferation level observed in the presence of exogenous Il-6. This confirms the capability of the PAC3 protein of the invention to significantly block the biological activity of IL-6 in particular the induction of tumoral proliferation induced by this exogenous IL-6.

Overall, these results indicate that the PAC3 protein of SEQ ID NO. 3 according to the invention blocks the proliferation of the U266 tumour line induced by exogenous IL-6, in the absence of IL-6, but above all considerably inhibits the proliferation of this line induced by exogenous IL-6. These results confirm the antagonist effect of the IL-6 of the PAC3 protein of SEQ ID NO. 3 according to the invention.

B.2—Differentiation of CD34+ Progenitors

B.2.1—Methods

Umbilical cord blood samples are diluted to ½ in PBS, then placed on a ficoll solution of density 1.077 to separate the different constituents of the sample by centrifugation according to density. The mononucleated cells being located at the interface, the ficoll is drawn off to purify the CD34+ by positive selection. Purification starts by marking with a mouse anti-CD34 monoclonal antibody (mouse IgG1 monoclonal antibody from Coulter, Marseille, France), then with a second goat anti-mouse F(ab')2 monoclonal antibody (Macs, Tebu, Paris, France) coupled to a magnetic bead. The formed complex is purified on a magnetic column.

After purification, the CD34+ progenitors are cultured from D0 to D6 in the presence of conventional RPMI 1640 supplemented with TNFα (2.5 ng/ml), GM-CSF (100 ng/ml), SCF (25 ng/ml) and human AB+ serum (2%) (EFS, Lyon, France). On D6, the CD34+ are washed three times in PBS to remove the AB+ serum, then cultured in the presence of TNFα (2.5 ng/ml), GM-CSF (100 ng/ml) and different concentrations of solution to be tested.

On D12, the cells are counted and washed, then left to incubate in the presence of fluorescent antibodies 20 min. at 4° C. After incubation, the cells are washed 3 times in PBS then analyzed by flow cytometry.

B.2.2—Results

The PAC3 protein of SEQ ID NO. 3 according to the invention exerts two types of activity on the differentiation of CD34+ progenitors in dendritic cells and in the presence GM-CSF and TNF α:

the first is an inhibiting action of the effect of IL-6 on the expression of DC differentiation membrane markers, in particular CD14, the second corresponds to partial blocking, by the PAC3 protein of SEQ ID NO.2, of CD1a acquisition by the cells being differentiated.

Figure 6:
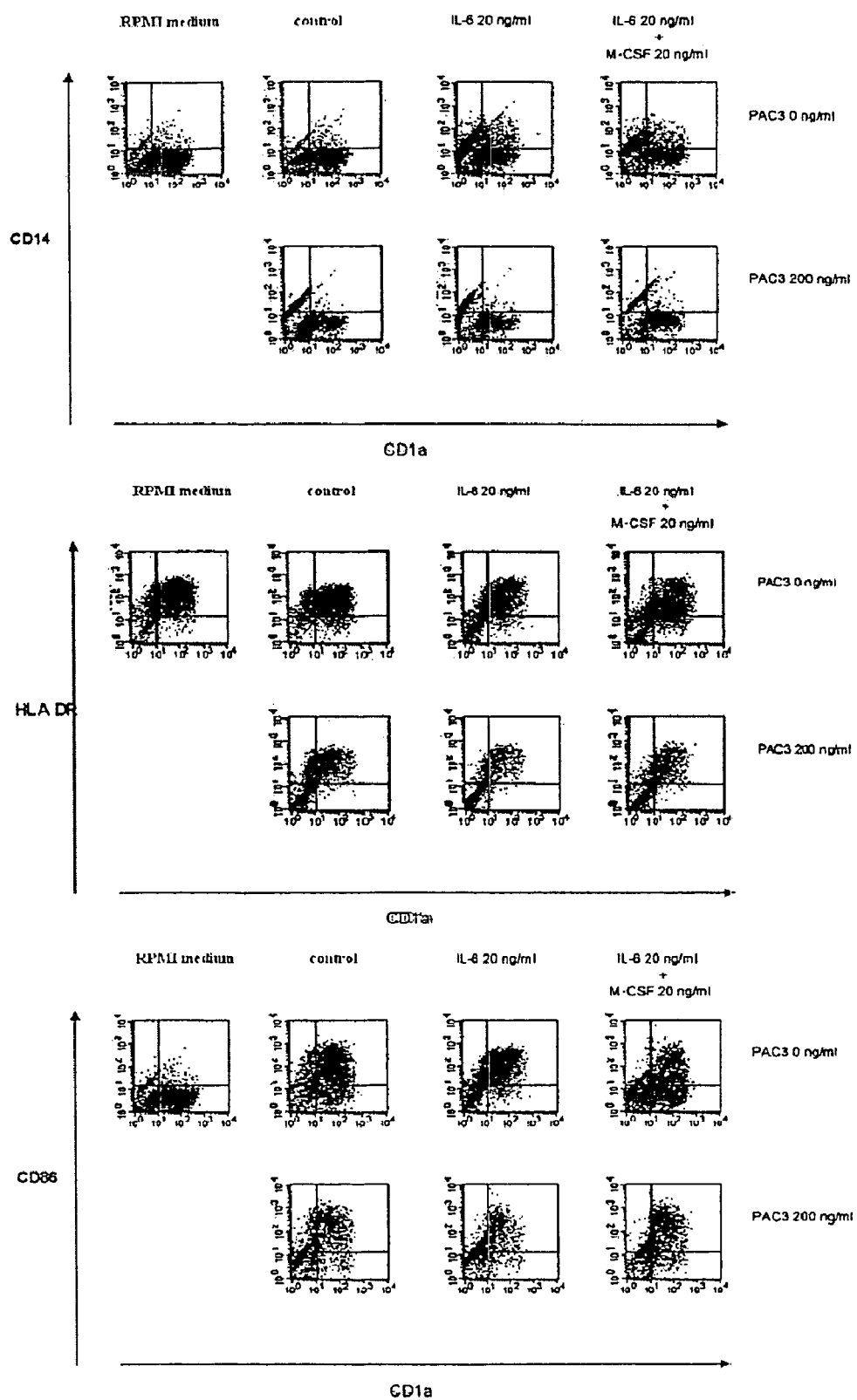

As shown by the results given in FIG. 6 the maintained expression of CD14 by IL-6, or IL-6 combined with M-CSF, is inhibited in the presence of the PAC3 protein of SEQ ID NO. 3. The same applies to the inhibition of CD86 expression induced by IL-6, or the combination of IL-6 and MCSF, which is partially restored in the presence of the PAC3 protein of SEQ ID NO. 3. These results confirm the inhibiting action of the PAC3 protein of SEQ ID NO. 3 on the biological activity of IL-6, in a pertinent model in man in clinical pathology, which is the blocking by IL-6 of DC differentiation from CD34+ progenitors.

The PAC3 protein of SEQ ID NO. 3 therefore affects the differentiation of the dendritic cells, orienting them towards a sub-population with weaker expression of the CD1a marker.

The PAC3 protein of SEQ ID NO. 3 also blocks the immunosuppressive effects of IL-6 in this model, in particular its capacity to inhibit normal differentiation of the dendritic cells.

B.3—Conclusions

The PAC3 protein of SEQ ID NO. 3 is therefore able to specifically block IL-6 induced proliferation of tumour cell lines, of the U266 myeloma line. The PAC3 protein of SEQ ID NO. 3 also blocks the ability of IL-6 to inhibit the differentiation of dendritic cells in vitro.

C—Production and Purification of the Protein of Sequence SEQ ID NO. 4

The position of the polyhistidine tail used for purification was changed. It was placed at the N-terminal of the protein to be cleaved by the TAGZyme system after purification.

C.1—Preparation of the Transfer Vector

The mutations are obtained using the KAE15.8 plasmid previously obtained and sequenced, on which PCR is performed using the pair of sequence primers:

- SEQ ID N° 17

GAG GGG ATC CAT GAA ACA CCA TCA CCA TCA CCA TGC

TAT GGC TGA AAA AGA TGG ATG CTT CCA ATC TGG

The SEQ ID NO. 17 sequence creates a BanHI restriction site at 5' and a poly-histidine tail compatible with the TAC-Zyme system of peptide sequence MKHHHHHHQ.

- SEQ ID N° 18

GGT GCG AAT TCT ACA TTT GCC GAA GAG CCC TC

The SEQ ID NO. 18 sequence creates a EcoRI restriction site at 3' after the stop codon.

PCR, fragment analysis and purification are conducted as previously described under items A.1. and A.2.

The digestion of purified PCR fragments and of the transfer plasmid pAcGP67-B is conducted using enzymes BamHI and EcoRI (Biolab) for 4 hour at 37° C. All the other construction steps of the baculovirus are similar to the steps described under items A.3.2 to A.3.3 above.

C.2—Production and Purification of the PAC3Bis Protein

C.2.1—Production

Production is made by infection of High Five cells (Invitrogen, France) in suspension. 1 l of EXPRESS FIVE SFM culture medium (Invitrogen, France) is seeded with $2.10^6$ cells.ml$^{-1}$ and 1 ml viral suspension with $10^8$ pfu.ml$^{-1}$. The whole is left to incubate for 7 days at 27° C., under gentle agitation. At the end of culture, the cells are residued by centrifugation at 10 000 g for 5 minutes and the supernatant is stored at 4° C.

C.2.2.1—Chromatography

The column is mounted on the Biorad HR chromatography system stabilized at 4° C. in a cold room. The flow rate of the column is limited to 3 ml.min$^{-1}$ with a maximum pressure of 150 psi.

Initially, the column is washed and activated with a first washing of 5 volumes of distilled water, then activated with 0.5 volume of 100 mM copper sulphate solution. The non-fixed copper is removed with 10 volumes of distilled water.

The column is stabilized with 10 volumes of 20 mM phosphate buffer pH=7.4, 1 M $NH_4Cl$.

Purification is conducted using several successive passes to avoid saturating the column.

Each passage starts with stabilisation of the U.V. base line at 280 nm using 2 volumes of 20 mM phosphate buffer pH=7.4, 1M $NH_4Cl$, then 4 volumes of dialysate are injected. A washing is performed with 6 volumes 20 mM phosphate buffer pH=7.4, 1M $NH_4Cl$.

Figure 7:
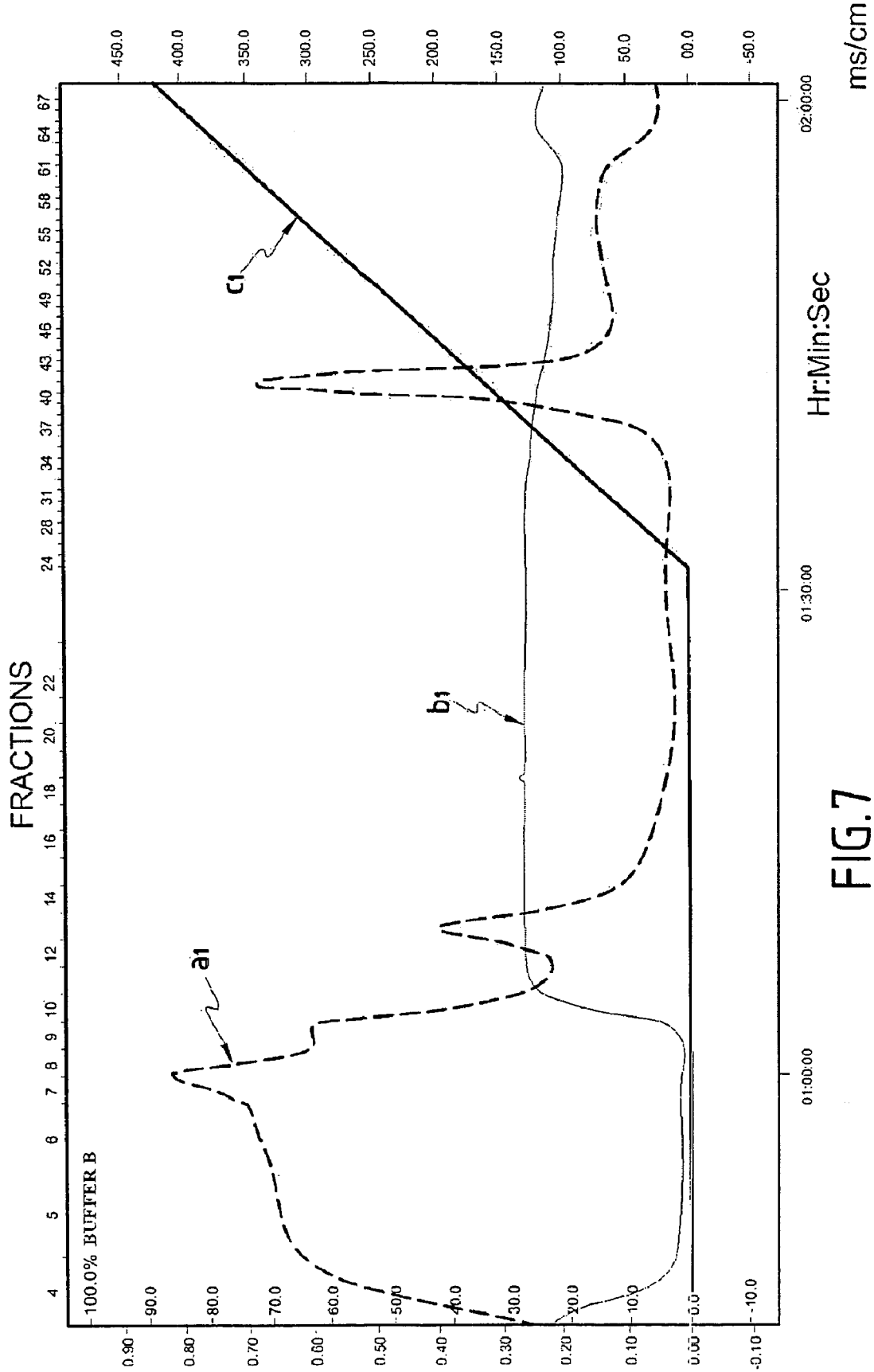
Figure 8A:
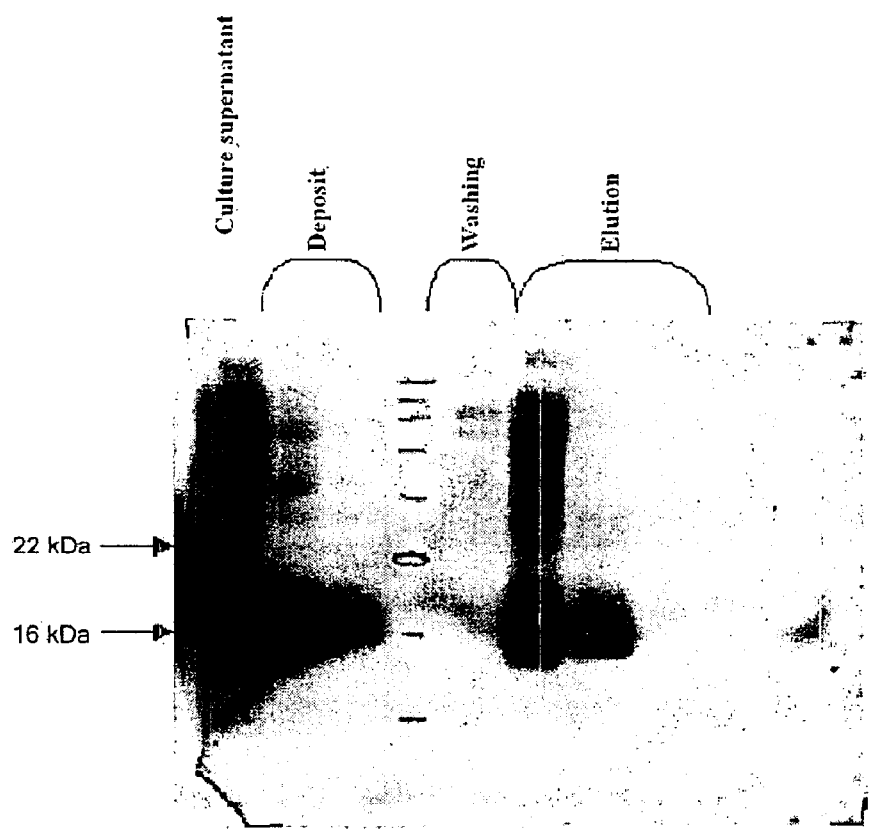
FIG. 8A is a Western Blot autoradiogram of the PAC3Bis protein.
Figure 8B:
FIG. 8B shows the same gel as in FIG. 8A but silver stained.

The proteins are eluted from the column using 4 volumes of a linear gradient, 0% to 60% 20 mM phosphate buffer pH=7.4, 500 mM NaCl, 500 mM d'imidazole. At the end of elution, the column is inactivated by injecting 6 volumes of 20 mM phosphate buffer pH=7.4, 500 mM EDTA then washed with 6 volumes of water. At this stage, the column can again be activated for further chromatography. The chromatography tracing is shown FIG. 7: curve $a_1$ gives absorbance at 280 nm, curve $b_1$ shows the conductivity of the solutions and curve $c_1$ the percentage of elution solution. Analysis of the chromatography fractions is made by Western Blot as described under item A.4. above. Different fractions are deposited on two SDS-page 15% acrylamide gels. After migration, the first is transferred onto a PVDF membrane for development using an anti-histidine antibody and chemiluminescence (FIG. 8A), while the second is silver stained (FIG. 8B).

C.2.3—Digestion of the Poly-Histidine Tail with the TAG-Zyme System

Once the fractions of interest have been identified, they are dialysed against 30 volumes of TAGyme digestion buffer (20 mM $NaH_2PO_4$, 1.5 M NaCl pH 7) through a dialysis membrane having a cut-off threshold of 8 Kda. After overnight dialysis at 4° C., under gentle agitation, the protein can then be concentrated with Centricon plus-20 then assayed by Biorad DC assay (Marne la Coquette, France).

Principle of the TAGZyme System:

The poly-histidine tail is cleaved from the protein by a succession of three enzymatic steps. During a first step, a di-peptidase (DAPase) cleaves di-peptides at the N-terminal of the protein stopping at a glutamine. During a second step, this glutamine is transformed by a Qcylase into a pyroglutamate, which is cleaved by a third enzyme pGAPase to obtain the native protein. All these three enzymes have a histidine tail at the C-terminal so that they can be extracted from the protein preparation after digestion.

5 mg of protein to be cleaved are incubated 15 minutes at 37° C. in the presence of 250 mU DAPaze activated by 10 mM cysteamine-HCl and 15 U Qcyclase. The digestion product is applied to a 1 ml NI-NTA agarose column previously washed with 5 volumes of TAGZyme digestion buffer. Once the digestion product has completely passed through the column, the column is washed a second time with two volumes of TAGZyme buffer. All the fractions passing through the column are harvested to be cleaved by a second incubation of 90 minutes at 37° C. in the presence of 1 mU pGAPase activated by 2 mM cysteamine-HCl. When digestion is finished, the protein preparation is purified a second time on a 1 ml NI-NTA column as previously described.

To make the protein preparation compatible with the biological test, it is dialysed against 20 volumes PBS without $Ca^{2+}$ and $Mg^{2+}$ through a dialysis membrane with a cut-off threshold of 8 kDa.

The digestion result is analysed using silver stained acrylamide gel and Western Blot as previously described under A.3.3.

Figure 9A:
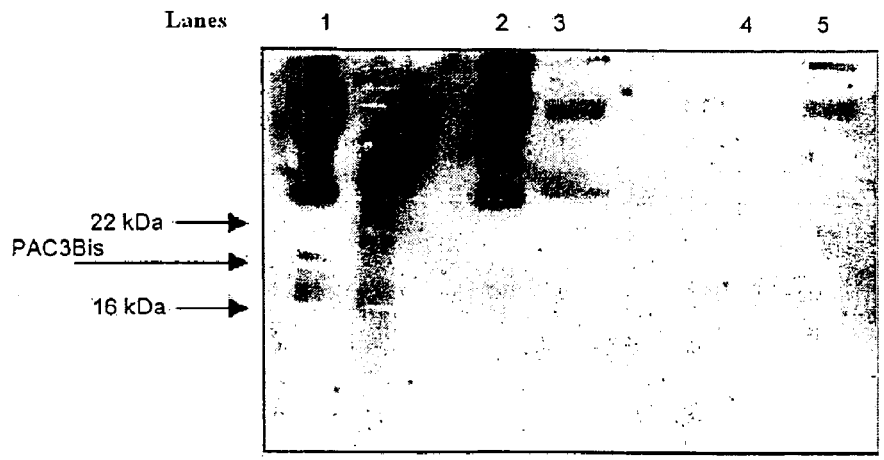
FIG. 9A shows Western Blot characterization of the different digestion steps of PAC3Bis pertinence.

FIG. 9A is a Western Blot autoradiogram developed by an anti-histidine antibody of the different digestion steps. In order of deposit are shown at 1) the non-digested protein, at 2) 3) the respective retentates of the 1° and 2° purification column, at 4) and 5) the respective eluates of the 1° and 2° purification column. The retentates of the purification columns clearly show that these columns capture a large part of the proteins having a poly-histidine tail (FIG. 9A: lanes 3 and 4) and the partly digested proteins (FIG. 9A: lane 3). Lanes 4 and 5 no longer show a poly-histidine protein with the expected molecular weight of PAC3Bis.

Figure 9B:
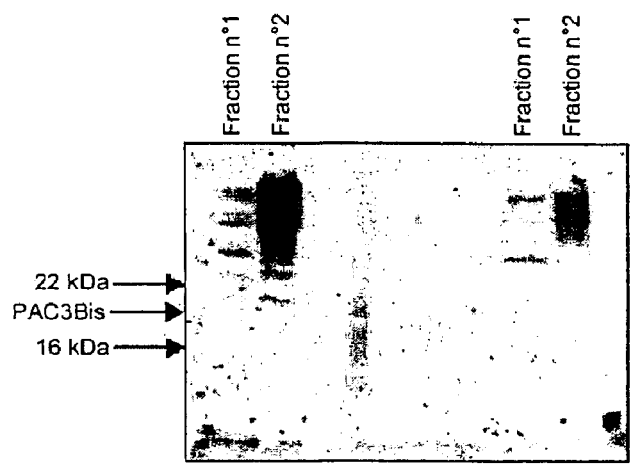
FIG. 9B is a Western Blot autoradiogram of fractions obtained after digestion.
Figure 9C:
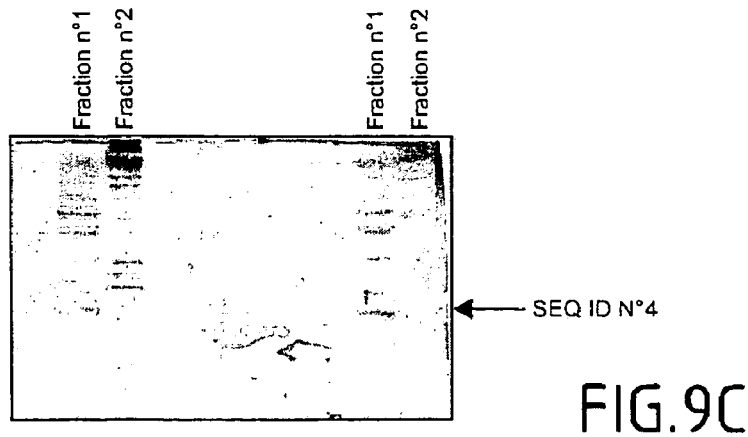
FIG. 9C shows the same fractions as in FIG. 9B but silver stained.

FIGS. 9B and 9C show two fractions of different purity of PAC3Bis before and after enzymatic digestion with the TAG-Zyme system under Westen Blot and after silver development respectively. The non-cleaved proteins are deposited on the left of the silver-developed gel or Western Blot autoradiogram, and the proteins after digestion are deposited on the right of the silver-developed gel or autoradiogram.

On these gels, it is possible to ascertain that even though no more poly-histidine marking is seen (photo on the right), the protein is still observed on a silver stained gel (left-side photo). These results show that the PAC3Bis protein is not deteriorated but it no longer has a poly-histidine tail and hence the sequence SEQ ID NO. 4.

D—Biological Activity

Inhibition of the Proliferation of Tumour Lines for which IL-6 Exerts a Mitogenic Effect.

The proliferation tests are identical to those mentioned under item B.1.

The U266 myeloma cells are incubated for 48 hours in the presence of increasing doses of PAC3Bis protein (SEQ ID NO.19) or protein of sequence SEQ ID NO.4. Cell proliferation is determined per 16 hours incorporation of tritiated thymidine. Results are expressed as percentage inhibition relative to a proliferation of U266 in the absence of PAC3Bis or of the protein of SEQ ID NO. 4.

RESULTS

The same rate of inhibition is observed with the PAC3Bis protein as with PAC3 on the proliferation of U266 in the absence of IL-6. The absence of a significant difference in inhibition in the presence (PAC3Bis) or not of the poly-histidine tail (SEQ ID NO. 4) shows that the poly-histidine tail does not interfere with the biological activity of the protein (FIG. 10).

SEQUENCE LISTING

```
<160> NUMBER OF SEQ ID NOS: 19

<210> SEQ ID NO 1
<211> LENGTH: 212
```

```
<212> TYPE: PRT
<213> ORGANISM: Homo sapiens

<400> SEQUENCE: 1

Met Asn Ser Phe Ser Thr Ser Ala Phe Gly Pro Val Ala Phe Ser Leu
 1               5                  10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
        50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 2
<211> LENGTH: 1125
<212> TYPE: DNA
<213> ORGANISM: Homo sapiens

<400> SEQUENCE: 2
ttctgccctc gagcccaccg ggaacgaaag agaagctcta tctcccctcc aggagcccag      60
ctatgaactc cttctccaca agcgccttcg gtccagttgc cttctccctg ggctgctcc     120 tggtgttgcc tgctgccttc ctgccccag taccccagg agaagattcc aaagatgtag      180
ccgccccaca cagacagcca ctcacctctt cagaacgaat tgacaaacaa attcggtaca     240
tcctcgacgg catctcagcc tgagaaaagg agacatgtaa caagagtaac atgtgtgaaa     300
gcagcaaaga ggcactggca gaaaacaacc tgaaccttcc aaagatggct gaaaaagatg     360
gatgcttcca atctggattc aatgaggaga cttgcctggt gaaaatcatc actggtcttt     420
tggagtttga ggtatacctta gagtacctcc agaacagatt tgagagtagt gaggaacaag     480
ccagagctgt gcagatgagt acaaaagtcc tgatccagtt cctgcagaaa aaggcaaaga     540
atctagatgc aataaccacc cctgacccaa ccacaaatgc cagcctgctg acgaagctgc     600
aggcacagaa ccagtggctg caggacatga caactcatct cattctgcgc agctttaagg     660
agttcctgca gtccagcctg agggctcttc ggcaaatgta gcatgggcac ctcagattgt     720
```

-continued

```
tgttgttaat gggcattcct tcttctggtc agaaacctgt ccactgggca cagaacttat    780
gttgttctct atggagaact aaaagtatga gcgttaggac actattttaa ttatttttaa    840
tttattaata tttaaatatg tgaagctgag ttaatttatg taagtcatat ttatatttt     900 aagaagtacc acttgaaaca ttttatgtat tagttttgaa ataataatgg aaagtggcta    960
tgcagtttga atatcctttg tttcagagcc agatcattc ttggaaagtg taggcttacc    1020
tcaaataaat ggctaactta tacatatttt taaagaaata tttatattgt atttatataa    1080
tgtataaatg gttttatac caataaatgg cattttaaaa aattc                    1125
```

<210> SEQ ID NO 3
<211> LENGTH: 125
<212> TYPE: PRT
<213> ORGANISM: Artificial Sequence
<220> FEATURE:
<223> OTHER INFORMATION: translation from 2nd ATG of exon 3 of the IL-6 gene, with polyhistidine tail

<400> SEQUENCE: 3

```
Met Ala Glu Lys Asp Gly Cys Phe Gln Ser Gly Phe Asn Glu Glu Thr
1               5                   10                  15

Cys Leu Val Lys Ile Ile Thr Gly Leu Leu Glu Phe Glu Val Tyr Leu
            20                  25                  30

Glu Tyr Leu Gln Asn Arg Phe Glu Ser Ser Glu Glu Gln Ala Arg Ala
        35                  40                  45

Val Gln Met Ser Thr Lys Val Leu Ile Gln Phe Leu Gln Lys Lys Ala
    50                  55                  60

Lys Asn Leu Asp Ala Ile Thr Thr Pro Asp Pro Thr Thr Asn Ala Ser
65                  70                  75                  80

Leu Leu Thr Lys Leu Gln Ala Gln Asn Gln Trp Leu Gln Asp Met Thr
                85                  90                  95

Thr His Leu Ile Leu Arg Ser Phe Lys Glu Phe Leu Gln Ser Ser Leu
            100                 105                 110

Arg Ala Leu Arg Gln Met Tyr His His His His His
        115                 120                 125
```

<210> SEQ ID NO 4
<211> LENGTH: 118
<212> TYPE: PRT
<213> ORGANISM: Artificial Sequence
<220> FEATURE:
<223> OTHER INFORMATION: translation from 2nd ATG of exon 3 of the IL-6 gene

<400> SEQUENCE: 4

```
Met Ala Glu Lys Asp Gly Cys Phe Gln Ser Gly Phe Asn Glu Glu Thr
1               5                   10                  15

Cys Leu Val Lys Ile Ile Thr Gly Leu Leu Glu Phe Glu Val Tyr Leu
            20                  25                  30

Glu Tyr Leu Gln Asn Arg Phe Glu Ser Ser Glu Glu Gln Ala Arg Ala
        35                  40                  45

Val Gln Met Ser Thr Lys Val Leu Ile Gln Phe Leu Gln Lys Lys Ala
    50                  55                  60

Lys Asn Leu Asp Ala Ile Thr Thr Pro Asp Pro Thr Thr Asn Ala Ser
65                  70                  75                  80

Leu Leu Thr Lys Leu Gln Ala Gln Asn Gln Trp Leu Gln Asp Met Thr
                85                  90                  95

Thr His Leu Ile Leu Arg Ser Phe Lys Glu Phe Leu Gln Ser Ser Leu
```

Arg Ala Leu Arg Gln Met
        115

<210> SEQ ID NO 5
<211> LENGTH: 33
<212> TYPE: DNA
<213> ORGANISM: Artificial Sequence
<220> FEATURE:
<223> OTHER INFORMATION: 5' primer creates a HinD III restriction site
      at 5' of first ATG of the IL-6 gene

<400> SEQUENCE: 5
gagaagcttt agcggccgcc caggagccca gct                                33

<210> SEQ ID NO 6
<211> LENGTH: 34
<212> TYPE: DNA
<213> ORGANISM: Artificial Sequence
<220> FEATURE:
<223> OTHER INFORMATION: 3' primer creates a Sma I restriction site at
      3' of the stop codon of the IL-6 gene

<400> SEQUENCE: 6
gaatgcccgg gaaactcgag aatctgaggt gccc                               34

<210> SEQ ID NO 7
<211> LENGTH: 27
<212> TYPE: DNA
<213> ORGANISM: Artificial Sequence
<220> FEATURE:
<223> OTHER INFORMATION: 5' primer which creates a BamHI restriction
      site at 5' of the second ATG of exon 3 of the IL-6 gene

<400> SEQUENCE: 7
ccttggatcc atggctgaaa aagatgg                                       27

<210> SEQ ID NO 8
<211> LENGTH: 48
<212> TYPE: DNA
<213> ORGANISM: Artificial Sequence
<220> FEATURE:
<223> OTHER INFORMATION: 3' primer which silences the stop codon of
      IL-6 then creates a tail of 6 histidines with a stop codon and a
      EcoR I restriction site on the stop codon

<400> SEQUENCE: 8
ggggaattct agtgatggtg atggtgatgg tacatttgcc gaagcccc                48

<210> SEQ ID NO 9
<211> LENGTH: 19
<212> TYPE: DNA
<213> ORGANISM: Artificial Sequence
<220> FEATURE:
<223> OTHER INFORMATION: sequence primer from base 30 in the reading
      direction of the IL-6 gene

<400> SEQUENCE: 9
agctatgaac tccttctcc                                                19

<210> SEQ ID NO 10
<211> LENGTH: 20
<212> TYPE: DNA
<213> ORGANISM: Artificial Sequence
<220> FEATURE:
<223> OTHER INFORMATION: sequence primer from base 187 on the
      complementary strand of the spliced IL-6 gene -continued

```
<400> SEQUENCE: 10
gttctgaaga ggtgagtggc                                              20

<210> SEQ ID NO 11
<211> LENGTH: 21
<212> TYPE: DNA
<213> ORGANISM: Artificial Sequence
<220> FEATURE:
<223> OTHER INFORMATION: sequence primer from base 401 in the reading
      direction of the IL-6 gene

<400> SEQUENCE: 11
aggtatacct agagtacctc c                                            21

<210> SEQ ID NO 12
<211> LENGTH: 20
<212> TYPE: DNA
<213> ORGANISM: Artificial Sequence
<220> FEATURE:
<223> OTHER INFORMATION: sequence primer from base 697 on the comple-
      mentary strand of the IL-6 gene

<400> SEQUENCE: 12
aactcgagaa tctgaggtgc                                              20

<210> SEQ ID NO 13
<211> LENGTH: 17
<212> TYPE: DNA
<213> ORGANISM: Artificial Sequence
<220> FEATURE:
<223> OTHER INFORMATION: sequence primer hybridizes at 5' of KS+ plasmid
      polylinker

<400> SEQUENCE: 13
tcgaggtcga cggtatc                                                 17

<210> SEQ ID NO 14
<211> LENGTH: 20
<212> TYPE: DNA
<213> ORGANISM: Artificial Sequence
<220> FEATURE:
<223> OTHER INFORMATION: sequence primer hybridizes at 3' of KS+ plasmid
      polylinker

<400> SEQUENCE: 14
gcgagatctt gatcacctag                                              20

<210> SEQ ID NO 15
<211> LENGTH: 22
<212> TYPE: DNA
<213> ORGANISM: Artificial Sequence
<220> FEATURE:
<223> OTHER INFORMATION: sequence primer hybridizes at 5' of KS+
      plasmid polylinker

<400> SEQUENCE: 15
gtaatacgac tcactatagg gc                                           22

<210> SEQ ID NO 16
<211> LENGTH: 20
<212> TYPE: DNA
<213> ORGANISM: Artificial Sequence
<220> FEATURE:
<223> OTHER INFORMATION: sequence primer from base 258 on the comple-
      mentary strand of the IL-6 gene
```

```
<400> SEQUENCE: 16
gcttgttcct cactactctc                                              20

<210> SEQ ID NO 17
<211> LENGTH: 69
<212> TYPE: DNA
<213> ORGANISM: Artificial Sequence
<220> FEATURE:
<223> OTHER INFORMATION: at 5' creates a BanHI restriction site and
      poly-histidine tail compatible with the TAGZyme system of peptide
      sequence MKHHHHHHQ

<400> SEQUENCE: 17
gaggggatcc atgaaacacc atcaccatca ccatgctatg gctgaaaaag atggatgctt   60
ccaatctgg                                                          69

<210> SEQ ID NO 18
<211> LENGTH: 32
<212> TYPE: DNA
<213> ORGANISM: Artificial Sequence
<220> FEATURE:
<223> OTHER INFORMATION: at 3' creates EcoRI restriction site after the
      stop codon

<400> SEQUENCE: 18
ggtgcgaatt ctacatttgc cgaagagccc tc                                32

<210> SEQ ID NO 19
<211> LENGTH: 127
<212> TYPE: PRT
<213> ORGANISM: Artificial Sequence
<220> FEATURE:
<223> OTHER INFORMATION: translation from 2nd ATG of exon 3 of the IL-6
      gene, with polyhistidine tail at N-terminal

<400> SEQUENCE: 19

Met Lys His His His His His His Gln Met Ala Glu Lys Asp Gly Cys
1               5                   10                  15

Phe Gln Ser Gly Phe Asn Glu Glu Thr Cys Leu Val Lys Ile Ile Thr
            20                  25                  30

Gly Leu Leu Glu Phe Glu Val Tyr Leu Glu Tyr Leu Gln Asn Arg Phe
        35                  40                  45

Glu Ser Ser Glu Glu Gln Ala Arg Ala Val Gln Met Ser Thr Lys Val
    50                  55                  60

Leu Ile Gln Phe Leu Gln Lys Lys Ala Lys Asn Leu Asp Ala Ile Thr
65                  70                  75                  80

Thr Pro Asp Pro Thr Thr Asn Ala Ser Leu Leu Thr Lys Leu Gln Ala
                85                  90                  95

Gln Asn Gln Trp Leu Gln Asp Met Thr Thr His Leu Ile Leu Arg Ser
            100                 105                 110

Phe Lys Glu Phe Leu Gln Ser Ser Leu Arg Ala Leu Arg Gln Met
        115                 120                 125
```

The invention claimed is:

1. An isolated protein consisting of the amino acid sequence of SEQ ID NO: 4.

2. A composition comprising a protein in association with a pharmaceutically acceptable excipient, said protein consisting of the amino acid sequence of SEQ ID NO: 4.

3. A composition according to claim 2 formulated for oral, sublingual, subcutaneous, intramuscular, intravenous, or topical administration.

* * * * *